(12) United States Patent
Sun et al.

(10) Patent No.: US 10,941,196 B2
(45) Date of Patent: Mar. 9, 2021

(54) ANTI-TNF-α FULLY HUMAN MONOCLONAL ANTIBODIES WITH LOW IMMUNOGENICITY AND APPLICATION THEREOF

(71) Applicant: ABMAX BIOTECHNOLOGY CO., LTD., Beijing (CN)

(72) Inventors: Le Sun, Beijing (CN); Xiaogang Zhang, Beijing (CN); Maohua Li, Beijing (CN); Cuijuan Zhang, Beijing (CN)

(73) Assignee: ABMAX BIOTECHNOLOGY CO., LTD., Beijing (CN)

( * ) Notice: Subject to any disclaimer, the term of this patent is extended or adjusted under 35 U.S.C. 154(b) by 2 days.

(21) Appl. No.: 15/502,777

(22) PCT Filed: Mar. 18, 2015

(86) PCT No.: PCT/CN2015/074528
§ 371 (c)(1),
(2) Date: Feb. 8, 2017

(87) PCT Pub. No.: WO2016/019726
PCT Pub. Date: Feb. 11, 2016

(65) Prior Publication Data
US 2017/0327570 A1    Nov. 16, 2017

(30) Foreign Application Priority Data
Aug. 8, 2014 (CN) .......................... 201410390493.4

(51) Int. Cl.
| | |
|---|---|
| C07K 16/24 | (2006.01) |
| G01N 33/577 | (2006.01) |
| G01N 33/68 | (2006.01) |
| A61K 39/395 | (2006.01) |
| A61K 39/00 | (2006.01) |

(52) U.S. Cl.
CPC .......... *C07K 16/241* (2013.01); *A61K 39/395* (2013.01); *C07K 16/24* (2013.01); *G01N 33/577* (2013.01); *G01N 33/68* (2013.01); *A61K 2039/505* (2013.01); *C07K 2317/21* (2013.01); *C07K 2317/51* (2013.01); *C07K 2317/515* (2013.01); *C07K 2317/565* (2013.01); *C07K 2317/567* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 2010/0266613 | A1 | 10/2010 | Harding et al. |
| 2015/0368335 | A1 | 12/2015 | Banerjee et al. |

FOREIGN PATENT DOCUMENTS

| | | | |
|---|---|---|---|
| CN | 102439040 A | 5/2012 | |
| CN | 102755646 A | 10/2012 | |
| WO | WO-2009083246 A1 * | 7/2009 | ........... C07K 16/241 |

OTHER PUBLICATIONS

Van Schouwenburg et al., Nature Reviews Rheumatology vol. 9, pp. 164-172 (2013). (Year: 2013).*
EP examination report dated Apr. 15, 2019 in conjunction with the EP equivalent to the instant application, pp. 1-4. (Year: 2019).*
International Search Report dated Jun. 29, 2015 in International Application No. PCT/CN2015/074528, filed Mar. 18, 2015, in 11 pages.

* cited by examiner

*Primary Examiner* — Zachary S Skelding
(74) *Attorney, Agent, or Firm* — Knobbe Martens Olson & Bear, LLP

(57) ABSTRACT

Disclosed herein are low immunogenic human anti-TNF-αantibodies which can inhibit the apopotosis of cells induced by TNF-α. The invented low immunogenic human anti-TNF-α antibodies are capable of binding to TNF-α specifically. The invention presents the human anti-TNF-αantibodies which bind to TNF-α with similar affinities as Adalimumab. Most importantly, the invented human anti-TNF-α antibodies showed reduced immunogenicities in vivo, which made them safer candidate for antibody drug and other biotherapy. The invention also features method of de-immunogenicity of antibody drugs by identification, replacement of high immunogenic FR sequence(s) of the human antibody with low immunogenic FR sequences from other human IgGs, and significantly reduce the risk of human anti-human immunogenicity and improve the efficacy of antibody drugs.

Figures 1, 2:
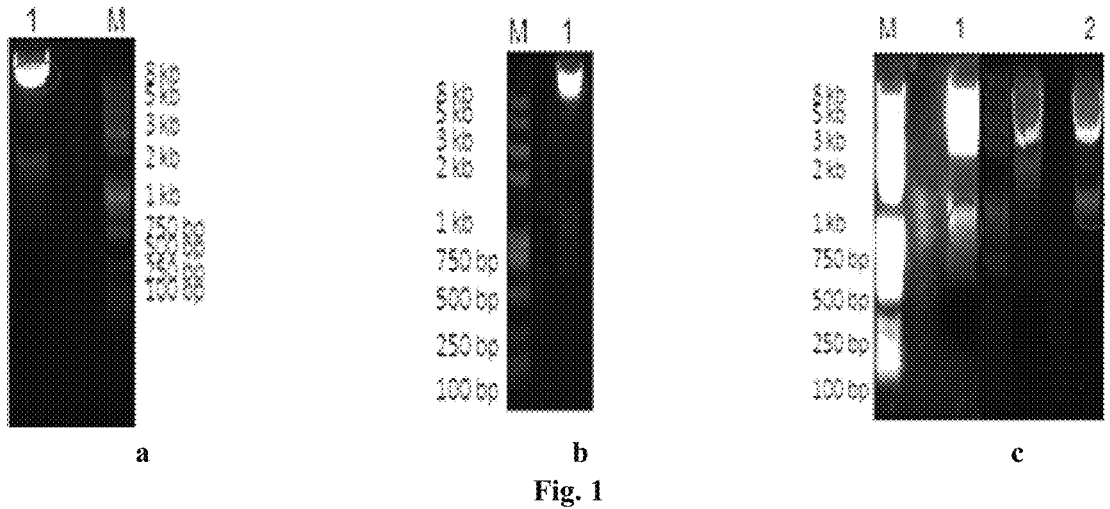
Figures 3, 4:
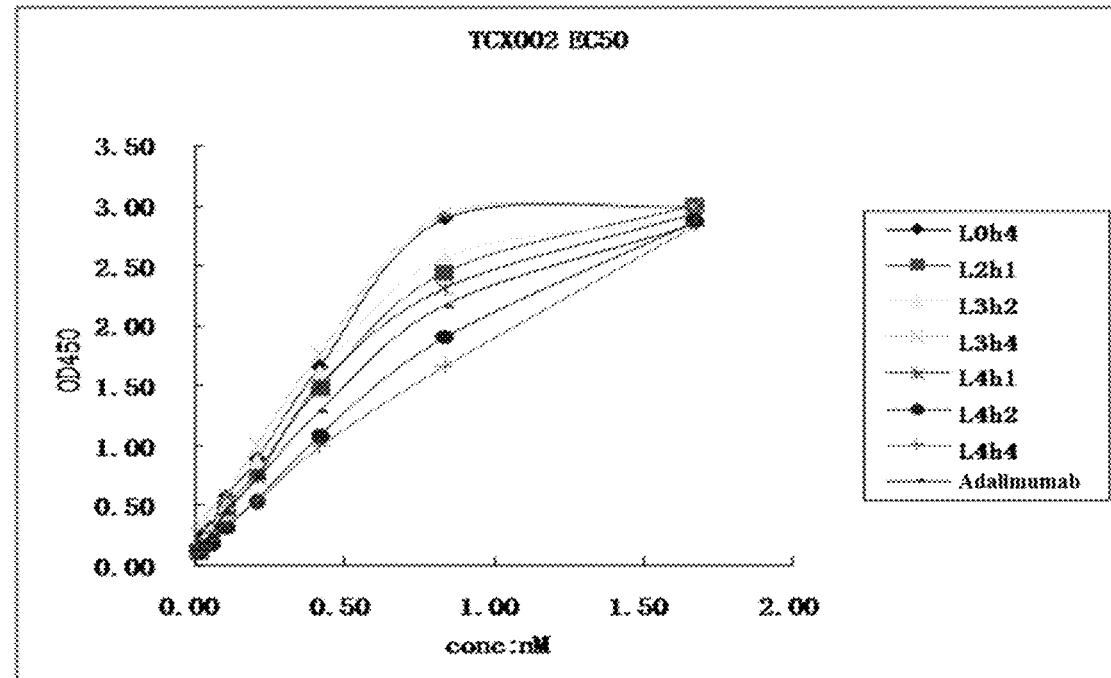

2 Claims, 3 Drawing Sheets
Specification includes a Sequence Listing.

ANTI-TNF-α FULLY HUMAN MONOCLONAL ANTIBODIES WITH LOW IMMUNOGENICITY AND APPLICATION THEREOF

REFERENCE TO SEQUENCE LISTING

A Sequence Listing submitted as an ASCII text file via EFS-Web is hereby incorporated by reference in accordance with 35 U.S.C. § 1.52(e). The name of the ASCII text file for the Sequence Listing is 31142945_1.TXT, the date of creation of the ASCII text file is Aug. 15, 2019, and the size of the ASCII text file is 32.2 KB.

TECHNICAL FIELD

The present invention relates to de-immunogenicity of anti-Tumor Necrosis Factor-alpha (TNF-α) antibodies and applications of using the same for treating inflammatory diseases and other human diseases.

BACKGROUND

TNF is an immunity-modulating cytokine required for immune processes. The unregulated activities of TNFs can lead to the development of inflammatory diseases. Excess amounts of TNF-expressed in cells are associated with the development of immune diseases, including rheumatoid arthritis, Crohn's disease, psoriatic arthritis, and inflammatory bowel disease. The function of TNF requires binding to its two receptors, TNF receptor 1 (TNFR1) and TNF receptor 2 (TNFR2). Blocking the interaction between TNF and TNFRs has successfully been developed as a therapy in treating inflammatory or autoimmune diseases. TNF neutralization therapies, including the use of a soluble TNFR2-Fc recombinant (Etanercept), a mouse-human chimera mAb (Infliximab), or a human mAb (Adalimumab), have been introduced in the past decades for the management of rheumatoid arthritis and other immune diseases.

However, although it is fully human antibody, high immunogenicity has been observed in human patients treated with Adalimumab. Anti-drug antibody (ADA) to Adalimumab was detected in up to 75% of the patients. It was also reported that the annual loss of response to Adalimumab was calculated to be 24%. ADA was considered as the causes of treatment failures, and it is believed that ADAs might reduce drug efficacy by competing with the endogenous ligand (neutralizing antibodies, Nab) and/or by forming immune complex, which accelerate the clearance of the drug from the circulation. Therefore there is need to develop a better anti-TNF antibody with lower immunogenicity and longer efficicay.

This invention is about the de-immunogenicity of human anti-Tumor Necrosis Factor-alpha (TNF-α) antibody Adalimumab, designed as clones TCX002-L3H4, L1H4. etc, which bind to the same epitope from the one recognized by Adalimumab, but with much lower immunogenicities in vivo.

SUMMARY OF THE INVENTION

The present invention provides the human anti-Tumor Necrosis Factor-alpha (TNF-α) antibodies with reduced immunogenicities and methods of using the same for neutralizing the TNF-α induced cell death and for treating inflammatory diseases and other human diseases. In one aspect, the present invention features TNF-α-binding molecules and their DNA and amino acid sequences. Each molecule comprises the CDRs from human anti-TNF-α monoclonal antibody Adalimumab and the FRs from different human origins.

The present invention also provides a method to develop human antibodies with reduced immunogenicities by replacing the FRs of the original human monoclonal antibody with the FRs from different human origins.

In addition, the present invention also provides one example of using the method to develop human anti-TNF-α antibodies with reduced immunogenicities by replacing the FRs of human anti-TNF-α monoclonal antibody Adalimumab with the FRs from different human origins.

The present invention features de-immunized human anti-TNF-α antibodies with one of the amino acid sequences of light chains shown in SEQ ID NO. 11~15 or 23, and one of the amino acid sequences of heavy chains shown in SEQ ID NO. 16~20.

Furthermore, the present invention features de-immunized human anti-TNF-α antibodies with one of the DNA sequences of light chains L1-L5 shown in SEQ ID NO. 1~5, and one of the DNA sequences of heavy chains h1-h5 shown in SEQ ID NO. 6~10.

Furthermore, the present invention features de-immunized human anti-TNF-α antibody with the the amino acid sequence of light chains shown in SEQ ID NO. 13, and the amino acid sequences of heavy chain shown in SEQ ID19.

Furthermore, the present invention features de-immunized human anti-TNF-α antibody with the DNA sequence of light chain shown in SEQ ID NO. 3, and the DNA sequence of heavy chain shown in SEQ ID. 9

The present invention provides the sequences for 10 de-immunized human anti-TNF-α antibodies, named as L3h2, L3h4, L5h2, L4h1, L4h2, L4h4, L1h3, L2h1, L0h4 and L2h5, which have similar affinities as the original and can block the binding of TNF-α to its receptors TNFRs p55 and p75.

Whereas, the de-immunized human anti-TNF-α antibody L3h2 with the amino acid sequence of light chains shown in SEQ ID NO. 13 and the amino acid sequences of heavy chain shown in SEQ ID No. 17, and with the DNA sequence of light chain shown in SEQ ID NO. 3, and the DNA sequence of heavy chain shown in SEQ ID No. 7.

Whereas, the de-immunized human anti-TNF-α antibody L3h4 with the amino acid sequence of light chains shown in SEQ ID NO. 13 and the amino acid sequences of heavy chain shown in SEQ ID No. 19 and with the DNA sequence of light chain shown in SEQ ID NO. 3, and the DNA sequence of heavy chain shown in SEQ ID No. 9.

Whereas, the de-immunized human anti-TNF-α antibody L5h2 with the amino acid sequence of light chains shown in SEQ ID NO. 15 and the amino acid sequences of heavy chain shown in SEQ ID No. 17, and with the DNA sequence of light chain shown in SEQ ID NO. 5, and the DNA sequence of heavy chain shown in SEQ ID No. 7.

Whereas, the de-immunized human anti-TNF-α antibody L4h1 with the amino acid sequence of light chains shown in SEQ ID NO. 14 and the amino acid sequences of heavy chain shown in SEQ ID No. 16, and with the DNA sequence of light chain shown in SEQ ID NO. 4, and the DNA sequence of heavy chain shown in SEQ ID No. 6.

Whereas, the de-immunized human anti-TNF-α antibody L4h2 with the amino acid sequence of light chains shown in SEQ ID NO. 14 and the amino acid sequences of heavy chain shown in SEQ ID No. 17, and with the DNA sequence of light chain shown in SEQ ID NO. 4, and the DNA sequence of heavy chain shown in SEQ ID No. 7.

Whereas, the de-immunized human anti-TNF-α antibody L4h4 with the amino acid sequence of light chains shown in SEQ ID NO. 14 and the amino acid sequences of heavy chain shown in SEQ ID No. 19, and with the DNA sequence of light chain shown in SEQ ID NO. 4, and the DNA sequence of heavy chain shown in SEQ ID No. 9.

Whereas, the de-immunized human anti-TNF-α antibody L1h3 with the amino acid sequence of light chains shown in SEQ ID NO. 11 and the amino acid sequences of heavy chain shown in SEQ ID No. 18, and with the DNA sequence of light chain shown in SEQ ID NO. 1, and the DNA sequence of heavy chain shown in SEQ ID No. 8.

Whereas, the de-immunized human anti-TNF-α antibody L2h1 with the amino acid sequence of light chains shown in SEQ ID NO. 12 and the amino acid sequences of heavy chain shown in SEQ ID No. 16, and with the DNA sequence of light chain shown in SEQ ID NO. 2, and the DNA sequence of heavy chain shown in SEQ ID No. 6.

Whereas, the de-immunized human anti-TNF-α antibody L2h5 with the amino acid sequence of light chains shown in SEQ ID NO. 12 and the amino acid sequences of heavy chain shown in SEQ ID No. 20, and with the DNA sequence of light chain shown in SEQ ID NO. 2, and the DNA sequence of heavy chain shown in SEQ ID No. 10.

Whereas, the de-immunized human anti-TNF-α antibody L0h4 with the amino acid sequence of light chains shown in SEQ ID NO. 23 and the amino acid sequences of heavy chain shown in SEQ ID No. 19, and with the DNA sequence of light chain shown in SEQ ID NO. 21, and the DNA sequence of heavy chain shown in SEQ ID No. 9.

The present invention features the expression plasmid containing the de-immunized anti-TNF-α antibody sequences.

The present invention also covers the plasmid, the host cells containing the de-immunized anti-TNF-α antibody sequences.

The invention also provides de-immunized anti-TNF-α antibodies for treatment of human diseases targeting TNF-α.

The TNF-α-binding molecules or antibodies of the present invention can be used to inhibit the death of cells.

In addition, the TNF-A-binding molecules or antibodies of the present invention can be used to treat human diseases including rheumatoid arthritis, Crohn's disease, psoriatic arthritis, and inflammatory bowel disease. These methods comprise administrating an effective amount of a TNF-α-binding molecule or antibody of the present invention to a subject in need thereof.

Furthermore, the present invention also features pharmaceutical and diagnostic compositions comprising a TNF-α-binding molecule or antibody of the present invention.

The present invention provides the method of de-immunogenicity of anti-TNF-α monoclonal antibody, including:

1. Analysis the FR sequences of anti-TNF-α monoclonal antibody Adalimumab and identify the sequences with high immunogenicities.
2. Align the FR sequences of anti-TNF-α monoclonal antibody Adalimumab against the ones of human IgGs in NCBI database, and find the ones with high homologies but lower immunogenicities.
3. Replace the high immunogenic FR sequence(s) of anti-TNF-α monoclonal antibody Adalimumab with low immunogenic FR sequences from other human antibodies.
4. Perform 3D structure modeling of the newly designed antibody sequences against the anti-TNF-α monoclonal antibody Adalimumab using Pymol program to identify the ones with closest resembling of the original antibody.
5. Once the variable region sequences confirmed, chemically synthesize both the rariable sequences with artificially added restriction enzyme sites (Kpn I and BamH I for light chain variable region, KpnI and AgeI for heavy chain variable region), ligate to vector pJH16 to obtain the expression plasmids for heavy chain and light chain of human antibody (Results see FIG. 1). Screen for positive clones after transformation by sequencing and restriction enzyme digestions.
6. Extract the plasmids using the kit from Qiagen following the instruction from the manufacturer.
7. Transient co-transfect the different combinations of the human light and heavy chain expression plasmids produced different human anti-TNF-α monoclonal antibodies with different expression levels and affinities for TNF-α(see FIG. 4).
8. Based on above data, a few combinations were selected to develop stable cell lines for over-expression of human anti-TNF-α.
9. The human anti-TNF-α monoclonal antibodies featured in this invention bind to the same antigenic eptiope as Adalimumab but with reduce immunogenicities and different 3D structures, longer half-lives, could be a better biotherapeutics.
10. The present invention features method to modify the immunogenicity of Adalimumab in human patients by replacing some of the amino acid sequences in Adalimumab with other human sequences.
11. The present invention provides examples to show the modified human anti-TNF-α monoclonal antibodies have similar affinities as Adalimumab but extend the half-lives with prolonger efficicacies.

BRIEF DESCRIPTION

FIG. 1 Digestions of Plasmids. 1-a, double digestions of pJH16 plasmid with Kpn I and Age I. 1-b, double digestions of pJH16 with Kpn I and BamH I. 1-c, lane 1, double digestions of the heavy chain of Adailimumab. Lane 2, double digestions of the light chain of Adalimumab. M, the DNA markers.

FIG. 2 Sequence blasts the light chains of the modified vs the one of Adalimumab.

FIG. 3 Sequence blasts the heavy chains of the modified vs the one of Adalimumab.

FIG. 4 The EC50s of modified human anti-TNF-α monoclonal antibodies.

FIG. 5 Inhibitions of TNF-α-induced cell toxicity in L929 cells by modified human anti-TNF-α monoclonal antibodies.

FIG. 6 PK study of modified human anti-TNF-α monoclonal antibodies.

DETAILED DESCRIPTION

It should be understood that the above-described embodiments and the following examples are given by way of illustration, not limitation. Various changes and modifications within the scope of the present invention will become apparent to those skilled in the art from the present description.

Unless specified, all the techniques used are common practices and can be performed by skilled personnel. All of the materials and reagents can be purchased commercially.

Example 1 Analysis and Modification of the Immunogenicity of the Sequences

Adalimumab

Used a program to examine the sequences of Adalimumab and found that the immunogenicity score is 16.

Used the same software to study the immunogenicities of the FRs of Adalimumab, identified the sequences with high immunogenicities, and searched human antibody sequence database for potential human sequences with lower immunogenicity.

Replaced the high immunogenic sequences in Adalimumab with the low immunogenic ones, and designed 5 human light chains L1-L5 (SEQ ID No. 1-5) and 5 human heavy chains h1-h5 (SEQ ID No. 6-10) for fully human anti-TNF-α monoclonal antibodies.

Perform 3D structure modeling of the newly designed antibody sequences against the ones of Adalimumab using Pymol program to identify the ones with closest resembling of the original antibody.

Fully human anti-TNF-α monoclonal antibodies can be any combination of one light chain from any one of L0-L5 (SEQ ID No. 1-5, 21) and one heavy chain from any one of h1-h5 (SEQ ID No. 6-10).

Example 2 Construction of the Expression Plasmids of Fully Human Anti-TNF-α Monoclonal Antibodies Added the restriction sites of Kpn I and BamH I to the light chain variable region sequences and the restriction sites of Kpn I and Age I to the heavy chain variable region sequences obtained in Example 1. All the variable region of the light and heavy chain sequences were inserted into the plasmids. Cut the heavy chain variable region sequences from the plasmids and inserted into the corresponding sites of the expression vector pJH16 using the restriction sites of Kpn I and Age I. Cut the light chain variable region sequences from the vector and inserted into the corresponding sites of the expression vector pJH16 using the restriction sites of Kpn I and BamH I, to obtain the fully human monoclonal antibody heavy and light chain expression plasmids. The plasmids and the expression vectors were subjected to enzyme digestions at 37 C overnight. Results of digestions of light chain, heavy chain, and the expression vectors are shown in FIG. 1. The bands of target genes and expression vectors were cut-out and extracted using Qiagen Gel Extraction Kit, then performed the ligations overnight using T4 DNA ligation system and transformed into E. coli DH5a. Colonies were picked for DNA sequencing and the alignments of sequencing data matched the designed gene 100%.

Example 3 Transient Expression and Purification of Fully Human Anti-TNF-α Monoclonal Antibodies Extracted the plasmids from the transformed E. coli DH5a, as shown in Example 2, using the Ultrapure Plasmid Prep kit from Qiagen.

Co-transfected the 293F cells with different combinations of the human light and heavy chain expression plasmids using lipofecting reagents from Invitogen. Total 31 combinations tried.

The expression levels of human IgGs in the culture supernants were examined on Day 3 and the expression levels ranged between 423.5-2624 ng/ml.

TABLE 1

| \multicolumn{12}{c}{Expression Levels of Human Antibodies (ng/ml)} |
| Comb. | Conc. | Comb. | Conc. | Comb. | Conc. | Comb. | Conc. | Comb. | Conc. | Comb. | Conc. |
| --- | --- | --- | --- | --- | --- | --- | --- | --- | --- | --- | --- |
| L0h1 | 1530 | L1h1 | 1371 | L2h1 | 1988 | L3h1 | 2624 | L4h1 | 810.7 | L5h1 | 439.1 |
| L0h2 | 11172 | L1h2 | 487.6 | L2h2 | 755.8 | L3h2 | 1208 | L4h2 | 1130 | L5h2 | 423.5 |
| L0h3 | 2021 | L1h3 | 873.3 | L2h3 | 662.2 | L3h3 | 602.9 | L4h3 | 2206 | L5h3 | 797 |
| L0h4 | 1109 | L1h4 | 1257 | L2h4 | 476 | L3h4 | 1638 | L4h4 | 1381 | L5h4 | 475.9 |
| L0h5 | 1408 | L1h5 | 868 | L2h5 | 677.7 | L3h5 | 1282 | L4h5 | 1423 | L5h5 | 952.2 |
| Adh010 | 1892 | | | | | | | | | | |

(Note: The table is a combination of different combinations of light and heavy chains. For example, L0h1 refers to the combination of light chain L0 from the adalimumab light chain variable region and the heavy chain h1 from a modified anti-TNF-α antibody.)

Performed indirect ELISA against TNF-α coated on 96-well plate, and found some of them (L0h4, L3h4, L3h2, L4h4, etc) have strong signals as Adalimumab, and some of them lost the binding affinity (L0h2) (Data see Table 2)

TABLE 2

ELISA Screening of Different Combinations against TNF-α

| | | | | | | | | | | | | |
|---|---|---|---|---|---|---|---|---|---|---|---|---|
| Comb. | L0h1 | | L0h2 | | L0h3 | | L0h4 | | L0h5 | | NC | |
| OD | 2.158 | 2.182 | 0.057 | 0.054 | 0.68 | 0.768 | 3.339 | 3.133 | 1.03 | 0.873 | 0.09 | 0.059 |
| Comb. | L1h1 | | L1h2 | | L1h3 | | L1h4 | | L1h5 | | NC | |
| OD | 1.926 | 2.401 | 2.268 | 2.459 | 1.413 | 1.431 | 2.621 | 2.552 | 0.824 | 1.051 | 0.045 | 0.057 |
| Comb. | L2h1 | | L2h2 | | L2h3 | | L2h4 | | L2h5 | | NC | |
| OD | 1.891 | 2.384 | 2.802 | 2.704 | 0.709 | 0.973 | 2.235 | 2.848 | 0.894 | 1.255 | 0.047 | 0.051 |
| Comb. | L3h1 | | L3h2 | | L3h3 | | L3h4 | | L3h5 | | L0h0 | |
| Comb. | 2.178 | 2.329 | 2.434 | 2.498 | 0.888 | 0.815 | 2.616 | 2.664 | 0.959 | 1.104 | 3.008 | 3.244 |
| OD | L4h1 | | L4h2 | | L4h3 | | L4h4 | | L4h5 | | L0h0 | |
| | 1.978 | 2.182 | 2.968 | 2.546 | 1.617 | 1.607 | 2.904 | 2.757 | 0.714 | 0.972 | 2.877 | 3.041 |
| Comb. | L5h1 | | L5h2 | | L5h3 | | L5h4 | | L5h5 | | L0h0 | |
| OD | 0.864 | 1.583 | 1.857 | 1.821 | 1.366 | 1.404 | 1.528 | 1.643 | 0.885 | 0.903 | 2.926 | 3.172 |

Example 4 Stable Expression and Purification of Fully Human Anti-TNF-α Monoclonal Antibodies Based on above data, 10 combinations were selected to develop stable cell lines for over-expression of human anti-TNF-α.

CHO cells was electro-transfected and selected under MTX pressure (purchased from Sigma) in the selective Opti-CHO medium (purchased from Invitrogen). Five selecting gradients were set as 50 nM, 100 nM, 200 nM, 400 nM and 800 nM. After each round, the expression levels of IgG in the culture supernatants on Day 7 were examined using Sandwich ELISA method. The results showed that stable expressions of IgGs were observed with all of the combinations but the levels were different (Table 3).

TABLE 3

IgG Levels of different combinations at different stages

| Comb. | opti-cho IgG (ng/ml) | 50 nM IgG (ng/ml) | 100 nM IgG (ng/ml) |
|---|---|---|---|
| adh010 | 30 | 134 | 346 |
| L3h2 | 92.7 | 122 | 237 |
| L3h4 | 87.4 | 251 | 367 |
| L5h2 | 30.8 | 129 | 452 |
| L4h1 | 104 | 176 | 258 |
| L4h2 | 127 | 318 | 523 |
| L4h4 | 72.5 | 939 | 734 |
| L1h3 | 97 | 160 | 270 |
| L2h1 | 64 | 208.6 | 471 |
| L0h4 | 30 | 389 | 598 |
| L2h5 | 29.2 | 226 | 476 |

When the process was complete, limiting dilution was performed for monoclonal cloning. Cells were seeded at 96-well plate and cultured at 37° C. 5% CO$_2$. 14 days later, 50 μl of supernatant was collected for antibody production testing using sandwich ELISA method. Clones with higher expressing levels were selected for further expansion.

Used a Protein-A affinity chromatography column to purify the human anti-TNF-α antibodies from the culture supernatants of the 11 stable cell lines. The concentrations of antibodies were determined by OD280/1.4. The purities of the antibodies were examined by SDS-PAGE analysis.

Example 5 Biological Activities of Human Anti-TNF-α Antibodies

1. Affinities: The EC50s of the newly invented human anti-TNF-α antibodies were compared with the one of Adalimumab using Indirect ELISA. The wells of 96-well plates were coated with 300 ng/ml of TNF-α in PBS overnight at 4 C. After wash, the wells were blocked with 5% skim milk in PBS for 1 hour at room temperature. Various concentrations of antibodies diluted in 5% skim milk-PBS were added to the wells and incubated for 1 hour at room temperature. After another wash, HRP-conjugated goat-anti-human IgG secondary antibodies were added and incubated for another 1 hour. After through wash, the substrates were added and the absorbances at 450 nm were measured. As shown in Table 4, some of the newly invented human anti-TNF-α antibodies have very similar EC50 as Adalimumab.

TABLE 4

EC50s of human anti-TNF-α antibodies

| | Comb. | | | | | | | |
|---|---|---|---|---|---|---|---|---|
| | 10h4 | 12h1 | 13h2 | 13h4 | 14h1 | 14h2 | 14h4 | adh010 |
| EC50(nM) | 0.37 | 0.43 | 0.40 | 0.34 | 0.47 | 0.60 | 0.69 | 0.49 |

2. Specificities: The specificities of the newly invented human anti-TNF-α antibodies were examined by Indirect ELISA against TNF-α and other cytokines. The wells of 96-well plates were coated with 1000 ng/ml of rhTNFα, rhTNFβ, rIFN γ, IL-1α, IL-1β, IL-2, IL-4 and IL-8 in PBS overnight at 4 C. After wash, the wells were blocked with 5% skim milk in PBS for 1 hour at room temperature. Different human anti-TNF-α antibodies diluted in 5% skim milk-PBS were added to the wells and incubated for 1 hour at room temperature. After another wash, HRP-conjugated goat-anti-human IgG secondary antibodies were added and incubated for another 1 hour. After through wash, the substrates were added and the absorbances at 450 nm were measured. As shown in Table 5, all of the newly invented human anti-TNF-α antibodies are very specific for TNF-α.

TABLE 5

Specificities of human anti-TNF-α antibodies

| Cytokine | Adalimumab | | L0h4 | | L2h1 | | L3h2 | | L3h4 | |
|---|---|---|---|---|---|---|---|---|---|---|
| rTNFα | 2.877 | 3.041 | 3.339 | 3.238 | 2.251 | 2.325 | 2.434 | 2.498 | 2.804 | 2.789 |
| rTNFβ | 0.097 | 0.089 | 0.058 | 0.064 | 0.081 | 0.082 | 0.071 | 0.065 | 0.064 | 0.071 |
| rINFγ | 0.082 | 0.078 | 0.062 | 0.068 | 0.065 | 0.071 | 0.057 | 0.068 | 0.068 | 0.065 |
| IL-1α | 0.059 | 0.065 | 0.080 | 0.072 | 0.057 | 0.062 | 0.064 | 0.072 | 0.072 | 0.077 |
| IL-1β | 0.067 | 0.058 | 0.059 | 0.068 | 0.063 | 0.071 | 0.059 | 0.073 | 0.068 | 0.063 |
| IL-2 | 0.053 | 0.059 | 0.074 | 0.069 | 0.073 | 0.075 | 0.067 | 0.061 | 0.069 | 0.073 |
| IL-4 | 0.049 | 0.05 | 0.055 | 0.049 | 0.072 | 0.069 | 0.078 | 0.069 | 0.059 | 0.062 |
| IL-8 | 0.063 | 0.057 | 0.067 | 0.060 | 0.058 | 0.061 | 0.069 | 0.074 | 0.060 | 0.058 |

| Cytokine | L4h1 | | L4h2 | | L4h4 | | NC | | NC | |
|---|---|---|---|---|---|---|---|---|---|---|
| rTNFα | 2.018 | 2.121 | 2.754 | 2.802 | 2.826 | 2.855 | 0.054 | 0.051 | 0.044 | 0.051 |
| rTNFβ | 0.065 | 0.064 | 0.082 | 0.071 | 0.064 | 0.071 | 0.068 | 0.065 | 0.058 | 0.055 |
| rINFγ | 0.068 | 0.068 | 0.071 | 0.067 | 0.068 | 0.065 | 0.052 | 0.057 | 0.054 | 0.061 |
| IL-1α | 0.072 | 0.072 | 0.062 | 0.064 | 0.072 | 0.077 | 0.058 | 0.063 | 0.052 | 0.053 |
| IL-1β | 0.073 | 0.068 | 0.071 | 0.069 | 0.068 | 0.063 | 0.069 | 0.063 | 0.059 | 0.061 |
| IL-2 | 0.061 | 0.069 | 0.075 | 0.067 | 0.069 | 0.073 | 0.049 | 0.052 | 0.059 | 0.062 |

TABLE 5-continued

Specificities of human anti-TNF-α antibodies

| IL-4 | 0.069 | 0.059 | 0.069 | 0.078 | 0.069 | 0.072 | 0.060 | 0.058 | 0.062 | 0.058 |
| IL-8 | 0.074 | 0.060 | 0.061 | 0.069 | 0.060 | 0.058 | 0.064 | 0.051 | 0.054 | 0.057 |

3. Inhibition of TNF-α induced apotosis.

L929 cells were seeded at 50,000 cells/well of 96-well plate in RPMI-1640-10% FBS and incubated at 37° C. 5% CO2. 4 hours later, discard the medium and added 100 μl/well of different concentrations of ADALIMUMAB or the invented human anti-TNF-α antibodies in RPMI-1640-10% FBS plus Actinomysin D 1 ug/ml at 37° C. 5% CO2. One day's later, the cell numbers in each well were determined by CKK assay.

Figure 5A:
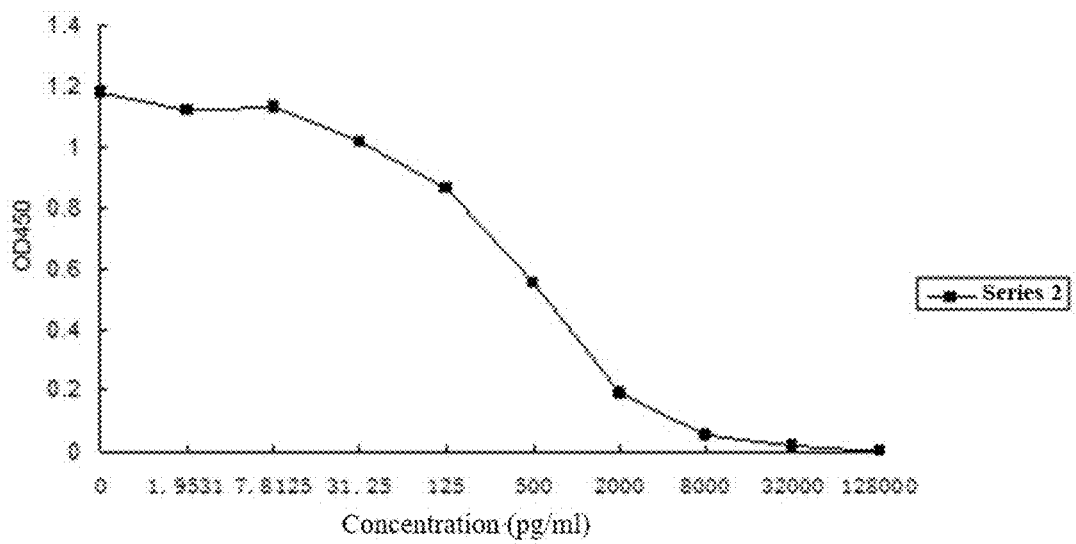
Figure 5B:
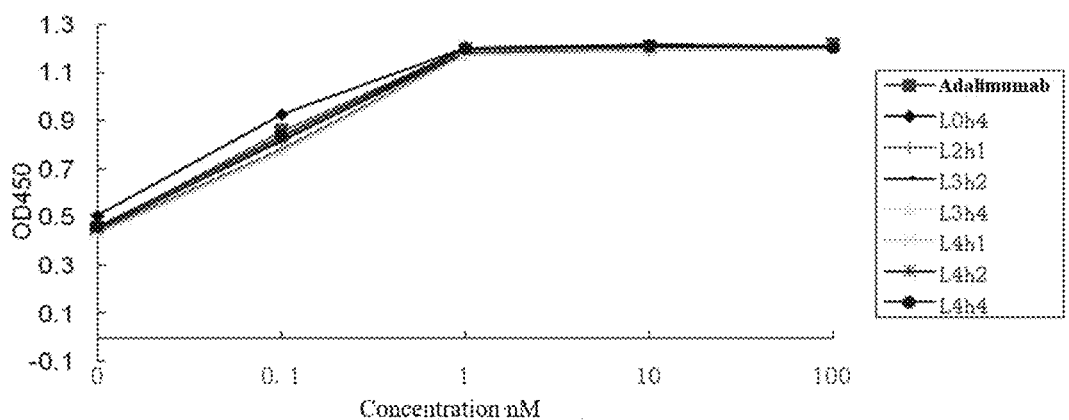

As shown in FIG. 5, both ADALIMUMAB and the newly invented human anti-TNF-α antibodies could inhibit TNF-α induced apoptosis of L929 cells.

Example 6 Immunogenicity and PK in Mice

1. Immunogenicity: Mice were injected with all 10 new human anti-TNF-α antibodies and Adalimumab with the adjuvant. 14 days' later, the tail bleeds were examined by ELISA against their antigens respectively. As shown in Table 6, the anti-drug antibody titers of some newly invented human anti-TNF-α antibodies were at least 5-time lower than the one of Adalimumab.

TABLE 6

ADA Titers of human anti-TNF-α antibodies in mice

|  |  | Titers | | | | | |
| --- | --- | --- | --- | --- | --- | --- | --- |
|  |  | 1:500 | 1:1000 | 1:5000 | 1:10000 | 1:50000 | NC |
| Comb. | L3h2 | 0.974 | 0.459 | 0.056 | 0.064 | 0.051 | 0.042 |
|  | L3h4 | 0.676 | 0.385 | 0.044 | 0.043 | 0.046 | 0.046 |
|  | L5h2 | 0.854 | 0.435 | 0.042 | 0.047 | 0.047 | 0.047 |
|  | L4h1 | 0.699 | 0.311 | 0.054 | 0.058 | 0.047 | 0.045 |
|  | L4h2 | 1.207 | 0.607 | 0.062 | 0.049 | 0.042 | 0.042 |
|  | L4h4 | 0.713 | 0.379 | 0.059 | 0.048 | 0.048 | 0.047 |

TABLE 6-continued

ADA Titers of human anti-TNF-α antibodies in mice

|  | Titers | | | | | |
| --- | --- | --- | --- | --- | --- | --- |
|  | 1:500 | 1:1000 | 1:5000 | 1:10000 | 1:50000 | NC |
| L0h4 | 1.016 | 0.591 | 0.048 | 0.067 | 0.054 | 0.056 |
| L1h3 | 1.156 | 0.548 | 0.043 | 0.080 | 0.053 | 0.055 |
| L2h1 | 0.781 | 0.389 | 0.041 | 0.056 | 0.059 | 0.057 |
| L2h5 | 0.802 | 0.410 | 0.032 | 0.066 | 0.053 | 0.047 |
| L0h0 | 2.614 | 1.311 | 0.2614 | 0.144 | 0.131 | 0.144 |

Figure 6:
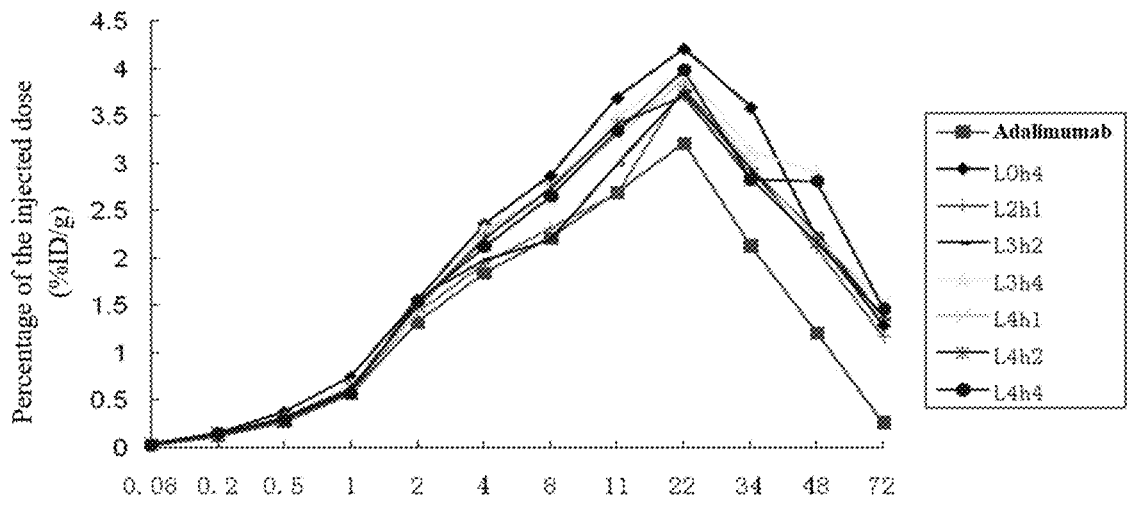

2. Pharmakintics: Mice were tail vent-injected with 125 I—labeled all 10 new human anti-TNF-α antibodies and Adalimumab (370 kBq, 2 μg), 5 mice per group. At various time points (5, 12, 30 min, 1, 2, 4, 8, 11, 22, 34, 48, 72 h), the blood samples were collected and the radioactivities were measured. As shown in FIG. 6, the PK of newly invented human anti-TNF-α antibodies were similar or better than the one of Adalimumab.

INDUSTRIAL APPLICATIONS

The invention features human anti-TNF-α antibodies which share the CDRs of the amino acid sequences from Adalimumab but with different FRs from other human IgGs. The newly invented human anti-TNF-α antibodies have the same specificities, similar affinities and inhibitory activities against TNF-α but much lower immunogenicities than Adalimumab. The invention also features method of de-immunogenicity of human antibodies by replacing the high immunogenic FR sequences with lower ones from other human IgGs without alter the activities of the antibody significantly. Reduced immunogenicity will significantly reduce the level of anti-drug antibody in the patients treated with anti-TNF-α drug, extend drug's half-life and increase the efficacy of the biological drugs.

What is claimed is:

1. A low immunogenic human anti-TNF-a antibody comprising the human light chain amino acid sequence of SEQ ID NO. 13 and the human heavy chain amino acid sequence of SEQ ID NO. 19.

2. A method for treating a disease selected from the group consisting of rheumatoid arthritis, Crohn's disease, psoriatic arthritis, and inflammatory bowel disease in a human, the method comprising administering the antibody of claim 1 to the human, thereby targeting TNF-α.

* * * * *

SEQUENCE LISTING

```
<160> NUMBER OF SEQ ID NOS: 24

<210> SEQ ID NO 1
<211> LENGTH: 714
<212> TYPE: DNA
<213> ORGANISM: Artificial sequence
<220> FEATURE:
<223> OTHER INFORMATION: Laboratory synthesis

<400> SEQUENCE: 1
atggacatga gggtccctgc tcagctcctg ggactcctgc tgctctggct cccagatacc      60
agatgtgaca tccagatgac ccagtctcca tcctccctgt ctgcatctgt aggagacaga     120
gtcaccatca cttgccgggc gagtcagggc attaggaatt atttagcctg gtatcagcag     180
aaaccaggga agctcctaa actcctgatc tatgctgcat ccactttgca atcagggtc       240 ccatctcggt tcagcggcag tggatctggg acaggtttca ctctcaccat cagcagcctg     300
cagcctgaag atgttgcaac ttattactgt caaaggtata cagagcccc gtacactttt      360
```

| | |
|---|---|
| ggccagggga ccaaggtgga gatcaaacga actgtggctg caccatctgt cttcatcttc | 420 |
| ccgccatctg atgagcagtt gaaatctgga actgcctctg ttgtgtgcct gctgaataac | 480 |
| ttctatccca gagaggccaa agtacagtgg aaggtggata acgccctcca atcgggtaac | 540 |
| tcccaggaga gtgtcacaga gcaggacagc aaggacagca cctacagcct cagcagcacc | 600 |
| ctgacgctga gcaaagcaga ctacgagaaa cacaaagtct acgcctgcga agtcacccat | 660 |
| cagggcctga gctcgcccgt cacaaagagc ttcaacaggg gagagtgtta gtaa | 714 |

```
<210> SEQ ID NO 2
<211> LENGTH: 714
<212> TYPE: DNA
<213> ORGANISM: Artificial sequence
<220> FEATURE:
<223> OTHER INFORMATION: Laboratory synthesis

<400> SEQUENCE: 2
```

| | |
|---|---|
| atggacatga gggtccctgc tcagctcctg ggactcctgc tgctctggct cccagatacc | 60 |
| agatgtgaca tccagatgac ccagtctcca tcctccctgt ctgcatctgt aggagacaga | 120 |
| gtcaccatca cttgccgggc gagtcagggc attaggaatt atttagcctg gtatcagcag | 180 |
| aaaccaggga aagctcctaa actcctgatc tatgctgcat ccactttgca atcaggggtc | 240 |
| ccatctcggt tcagcggcag tggatctggg acaggtttca ctctcaccat cagcagcctg | 300 |
| cagcctgaag attttgcaac ttattactgt caaaggtata acagagcccc gtacactttt | 360 |
| ggccagggga ccaaggtgga gatcaaacga actgtggctg caccatctgt cttcatcttc | 420 |
| ccgccatctg atgagcagtt gaaatctgga actgcctctg ttgtgtgcct gctgaataac | 480 |
| ttctatccca gagaggccaa agtacagtgg aaggtggata acgccctcca atcgggtaac | 540 |
| tcccaggaga gtgtcacaga gcaggacagc aaggacagca cctacagcct cagcagcacc | 600 |
| ctgacgctga gcaaagcaga ctacgagaaa cacaaagtct acgcctgcga agtcacccat | 660 |
| cagggcctga gctcgcccgt cacaaagagc ttcaacaggg gagagtgtta gtaa | 714 |

```
<210> SEQ ID NO 3
<211> LENGTH: 714
<212> TYPE: DNA
<213> ORGANISM: Artificial sequence
<220> FEATURE:
<223> OTHER INFORMATION: Laboratory synthesis

<400> SEQUENCE: 3
```

| | |
|---|---|
| atggacatga gggtccctgc tcagctcctg ggactcctgc tgctctggct cccagatacc | 60 |
| agatgtgaca tccagatgac ccagtctcca tcctccgtgt ctgcatctgt aggagacaga | 120 |
| gtcaccatca cttgccgggc gagtcagggc attaggaatt atttagcctg gtatcagcag | 180 |
| aaaccaggga aagctcctaa actcctgatc tatgctgcat ccactttgca atcaggggtc | 240 |
| ccatctcggt tcagcggcag tggatctggg acaggtttca ctctcaccat cagcagcctg | 300 |
| cagcctgaag atgttgcaac ttattactgt caaaggtata acagagcccc gtacactttt | 360 |
| ggccagggga ccaaggtgga gatcaaacga actgtggctg caccatctgt cttcatcttc | 420 |
| ccgccatctg atgagcagtt gaaatctgga actgcctctg ttgtgtgcct gctgaataac | 480 |
| ttctatccca gagaggccaa agtacagtgg aaggtggata acgccctcca atcgggtaac | 540 |
| tcccaggaga gtgtcacaga gcaggacagc aaggacagca cctacagcct cagcagcacc | 600 |
| ctgacgctga gcaaagcaga ctacgagaaa cacaaagtct acgcctgcga agtcacccat | 660 |
| cagggcctga gctcgcccgt cacaaagagc ttcaacaggg gagagtgtta gtaa | 714 |

<210> SEQ ID NO 4
<211> LENGTH: 714
<212> TYPE: DNA
<213> ORGANISM: Artificial sequence
<220> FEATURE:
<223> OTHER INFORMATION: Laboratory synthesis

<400> SEQUENCE: 4

| | |
|---|---|
| atggacatga gggtccctgc tcagctcctg ggactcctgc tgctctggct cccagatacc | 60 |
| agatgtgaca tccagatgac ccagtctcca tcctccgtgt ctgcatctgt aggagacaga | 120 |
| gtcaccatca cttgccgggc gagtcagggc attaggaatt atttagcctg gtatcagcag | 180 |
| aaaccaggga agctcctaa actcctgatc tatgctgcat ccactttgca atcaggggtc | 240 |
| ccatctcggt tcagcggcag tggatctggg acaggtttca ctctcaccat cagcagcctg | 300 |
| cagcctgaag attttgcaac ttattactgt caaaggtata acagagcccc gtacactttt | 360 |
| ggccagggga ccaaggtgga gatcaaacga actgtggctg caccatctgt cttcatcttc | 420 |
| ccgccatctg atgagcagtt gaaatctgga actgcctctg ttgtgtgcct gctgaataac | 480 |
| ttctatccca gagaggccaa agtacagtgg aaggtggata acgccctcca atcgggtaac | 540 |
| tcccaggaga gtgtcacaga gcaggacagc aaggacagca cctacagcct cagcagcacc | 600 |
| ctgacgctga gcaaagcaga ctacgagaaa cacaaagtct acgcctgcga agtcacccat | 660 |
| cagggcctga gctcgcccgt cacaaagagc ttcaacaggg gagagtgtta gtaa | 714 |

<210> SEQ ID NO 5
<211> LENGTH: 714
<212> TYPE: DNA
<213> ORGANISM: Artificial sequence
<220> FEATURE:
<223> OTHER INFORMATION: Laboratory synthesis

<400> SEQUENCE: 5

| | |
|---|---|
| atggacatga gggtccctgc tcagctcctg ggactcctgc tgctctggct cccagatacc | 60 |
| agatgtgaca tccagatgac ccagtctcca tcctccgtgt ctgcatctgt aggagacaga | 120 |
| gtcaccatca cttgccgggc gagtcagggc attaggaatt atttagcctg gtatcagcag | 180 |
| aaaccaggga aagtgcctgt actcctgatc tatgctgcat ccactttgca atcaggggtc | 240 |
| ccatctcggt tcagcggcag tggatctggg acaggtttca ctctcaccat cagcagcctg | 300 |
| cagcctgaag atgttgcaac ttattactgt caaaggtata acagagcccc gtacactttt | 360 |
| ggccagggga ccaaggtgga gatcaaacga actgtggctg caccatctgt cttcatcttc | 420 |
| ccgccatctg atgagcagtt gaaatctgga actgcctctg ttgtgtgcct gctgaataac | 480 |
| ttctatccca gagaggccaa agtacagtgg aaggtggata acgccctcca atcgggtaac | 540 |
| tcccaggaga gtgtcacaga gcaggacagc aaggacagca cctacagcct cagcagcacc | 600 |
| ctgacgctga gcaaagcaga ctacgagaaa cacaaagtct acgcctgcga agtcacccat | 660 |
| cagggcctga gctcgcccgt cacaaagagc ttcaacaggg gagagtgtta gtaa | 714 |

<210> SEQ ID NO 6
<211> LENGTH: 522
<212> TYPE: DNA
<213> ORGANISM: Artificial sequence
<220> FEATURE:
<223> OTHER INFORMATION: Laboratory synthesis

<400> SEQUENCE: 6

-continued

```
atggagttgg gactgagctg gattttcctt ttggctattt taaaaggtgt ccagtgtgag      60
gtgcagctgg tggagtctgg gggaggcttg gtacagcccg gcaggtccct gagactctcc     120
tgtgcggcct ctggattcac ctttgatgat tatgccatgc actgggtccg gcaagctcca    180
gggaagggcc tggaatgggt ctcagctatc acttggaata gtggtcacat agactatgcg    240
gactctgtgg agggccgatt caccatctcc ctggacacct ccaagtccac cgcttatctg    300
caaatgaaca gtctgagagc tgaggattca gccgtatatt actgtgcgaa agtctcgtac    360
cttagcaccg cgtcctccct tgactattgg ggccaaggaa ccctggtcac cgtctcgagt    420
gcctccacca agggcccatc ggtcttcccc ctggcaccct cctccaagag cacctctggg    480
ggcacagcag ccctgggctg cctggtcaag gactacttcc cc                       522
```

<210> SEQ ID NO 7
<211> LENGTH: 522
<212> TYPE: DNA
<213> ORGANISM: Artificial sequence
<220> FEATURE:
<223> OTHER INFORMATION: Laboratory synthesis

<400> SEQUENCE: 7

```
atggagttgg gactgagctg gattttcctt ttggctattt taaaaggtgt ccagtgtgag      60
gtgcagctgg tggagtctgg gggaggcttg gtacagcccg gcaggtccct gagactctcc     120
tgtgcggcct ctggattcac ctttgatgat tatgccatgc actgggtccg gcaagctcca    180
gggaagggcc tggaatgggt ctcagctatc acttggaata gtggtcacat agactatgcg    240
gactctgtgg agggccgatt caccttctcc ctggacacct ccaagtccac cgcttatctg    300
caaatgaaca gtctgagagc tgaggatacg gccgtatatt actgtgcgaa agtctcgtac    360
cttagcaccg cgtcctccct tgactattgg ggccaaggaa ccctggtcac cgtctcgagt    420
gcctccacca agggcccatc ggtcttcccc ctggcaccct cctccaagag cacctctggg    480
ggcacagcag ccctgggctg cctggtcaag gactacttcc cc                       522
```

<210> SEQ ID NO 8
<211> LENGTH: 522
<212> TYPE: DNA
<213> ORGANISM: Artificial sequence
<220> FEATURE:
<223> OTHER INFORMATION: Laboratory synthesis

<400> SEQUENCE: 8

```
atggagttgg gactgagctg gattttcctt ttggctattt taaaaggtgt ccagtgtgag      60
gtgcagctgg tggagtctgg gggaggcttg gtacagcccg gcggatccct gagactctcc    120
tgtgcggcct ctggatacac ctttgatgat tatgccatgc actgggtccg gcaagctcca    180
gggaagggcc tggaatgggt ctcagctatc acttggaata gtggtcacat agactatgcg    240
gactctgtgg agggccgatt caccatctcc ctggacacct ccaagtccac cgcttatctg    300
caaatgaaca gtctgagagc tgaggattca gccgtatatt actgtgcgaa agtctcgtac    360
cttagcaccg cgtcctccct tgactattgg ggccaaggaa ccctggtcac cgtctcgagt    420
gcctccacca agggcccatc ggtcttcccc ctggcaccct cctccaagag cacctctggg    480
ggcacagcag ccctgggctg cctggtcaag gactacttcc cc                       522
```

<210> SEQ ID NO 9
<211> LENGTH: 522
<212> TYPE: DNA
<213> ORGANISM: Artificial sequence
<220> FEATURE:
<223> OTHER INFORMATION: Laboratory synthesis

<400> SEQUENCE: 9

```
atggagttgg gactgagctg gattttcctt ttggctattt taaaaggtgt ccagtgtgag      60
gtgcagctgg tggagtctgg gggaggcttg gtacagcccg gcggatccct gagactctcc     120
tgtgcggcct ctggatacac ctttgatgat tatgccatgc actgggtccg gcaagctcca     180
gggaagggcc tggaatgggt ctcagctatc acttggaata gtggtcacat agactatgcg     240
gactctgtgg agggccgatt caccttctcc ctggacacct ccaagtccac cgcttatctg     300
caaatgaaca gtctgagagc tgaggatacg gccgtatatt actgtgcgaa agtctcgtac     360
cttagcaccg cgtcctccct tgactattgg ggccaaggaa ccctggtcac cgtctcgagt     420
gcctccacca agggcccatc ggtcttcccc ctggcaccct cctccaagag cacctctggg     480
ggcacagcag ccctgggctg cctggtcaag gactacttcc cc                        522
```

<210> SEQ ID NO 10
<211> LENGTH: 522
<212> TYPE: DNA
<213> ORGANISM: Artificial sequence
<220> FEATURE:
<223> OTHER INFORMATION: Laboratory synthesis

<400> SEQUENCE: 10

```
atggagttgg gactgagctg gattttcctt ttggctattt taaaaggtgt ccagtgtgag      60
gtgcagctgg tggagtctgg gggaggcttg gtacagcccg gcggatccct gagactctcc     120
tgtgcggcct ctggatacac ctttgatgat tatgccatgc actgggtccg gcaagctcca     180
gggaagggcc tggaatgggt ctcagctatc acttggaata gtggtcacat agactatgcg     240
gactctgtgg agggccgatt caccatctcc ctggacacct ccgtatccac cgcttatctg     300
caaatgaaca gtctgagagc tgaggattca gccgtatatt actgtgcgaa agtctcgtac     360
cttagcaccg cgtcctccct tgactattgg ggccaaggaa ccctggtcac cgtctcgagt     420
gcctccacca agggcccatc ggtcttcccc ctggcaccct cctccaagag cacctctggg     480
ggcacagcag ccctgggctg cctggtcaag gactacttcc cc                        522
```

<210> SEQ ID NO 11
<211> LENGTH: 236
<212> TYPE: PRT
<213> ORGANISM: Artificial sequence
<220> FEATURE:
<223> OTHER INFORMATION: Laboratory synthesis

<400> SEQUENCE: 11

```
Met Asp Met Arg Val Pro Ala Gln Leu Leu Gly Leu Leu Leu Leu Trp
  1               5                  10                  15
Leu Pro Asp Thr Arg Cys Asp Ile Gln Met Thr Gln Ser Pro Ser Ser
                 20                  25                  30
Leu Ser Ala Ser Val Gly Asp Arg Val Thr Ile Thr Cys Arg Ala Ser
             35                  40                  45
Gln Gly Ile Arg Asn Tyr Leu Ala Trp Tyr Gln Gln Lys Pro Gly Lys
         50                  55                  60
Ala Pro Lys Leu Leu Ile Tyr Ala Ala Ser Thr Leu Gln Ser Gly Val
 65                  70                  75                  80
Pro Ser Arg Phe Ser Gly Ser Gly Ser Gly Thr Gly Phe Thr Leu Thr
                 85                  90                  95
```

```
Ile Ser Ser Leu Gln Pro Glu Asp Val Ala Thr Tyr Tyr Cys Gln Arg
                100                 105                 110

Tyr Asn Arg Ala Pro Tyr Thr Phe Gly Gln Gly Thr Lys Val Glu Ile
            115                 120                 125

Lys Arg Thr Val Ala Ala Pro Ser Val Phe Ile Phe Pro Pro Ser Asp
130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
    210                 215                 220

Ser Pro Val Thr Lys Ser Phe Asn Arg Gly Glu Cys
225                 230                 235

<210> SEQ ID NO 12
<211> LENGTH: 236
<212> TYPE: PRT
<213> ORGANISM: Artificial sequence
<220> FEATURE:
<223> OTHER INFORMATION: Laboratory synthesis

<400> SEQUENCE: 12

Met Asp Met Arg Val Pro Ala Gln Leu Leu Gly Leu Leu Leu Leu Trp
1               5                   10                  15

Leu Pro Asp Thr Arg Cys Asp Ile Gln Met Thr Gln Ser Pro Ser Ser
                20                  25                  30

Leu Ser Ala Ser Val Gly Asp Arg Val Thr Ile Thr Cys Arg Ala Ser
            35                  40                  45

Gln Gly Ile Arg Asn Tyr Leu Ala Trp Tyr Gln Gln Lys Pro Gly Lys
    50                  55                  60

Ala Pro Lys Leu Leu Ile Tyr Ala Ala Ser Thr Leu Gln Ser Gly Val
65                  70                  75                  80

Pro Ser Arg Phe Ser Gly Ser Gly Ser Gly Thr Gly Phe Thr Leu Thr
                85                  90                  95

Ile Ser Ser Leu Gln Pro Glu Asp Phe Ala Thr Tyr Tyr Cys Gln Arg
                100                 105                 110

Tyr Asn Arg Ala Pro Tyr Thr Phe Gly Gln Gly Thr Lys Val Glu Ile
            115                 120                 125

Lys Arg Thr Val Ala Ala Pro Ser Val Phe Ile Phe Pro Pro Ser Asp
130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
    210                 215                 220
```

```
Ser Pro Val Thr Lys Ser Phe Asn Arg Gly Glu Cys
225                 230                 235

<210> SEQ ID NO 13
<211> LENGTH: 236
<212> TYPE: PRT
<213> ORGANISM: Artificial sequence
<220> FEATURE:
<223> OTHER INFORMATION: Laboratory synthesis

<400> SEQUENCE: 13

Met Asp Met Arg Val Pro Ala Gln Leu Leu Gly Leu Leu Leu Leu Trp
1               5                   10                  15

Leu Pro Asp Thr Arg Cys Asp Ile Gln Met Thr Gln Ser Pro Ser Ser
                20                  25                  30

Val Ser Ala Ser Val Gly Asp Arg Val Thr Ile Thr Cys Arg Ala Ser
            35                  40                  45

Gln Gly Ile Arg Asn Tyr Leu Ala Trp Tyr Gln Gln Lys Pro Gly Lys
        50                  55                  60

Ala Pro Lys Leu Leu Ile Tyr Ala Ala Ser Thr Leu Gln Ser Gly Val
65                  70                  75                  80

Pro Ser Arg Phe Ser Gly Ser Gly Ser Gly Thr Gly Phe Thr Leu Thr
                85                  90                  95

Ile Ser Ser Leu Gln Pro Glu Asp Val Ala Thr Tyr Tyr Cys Gln Arg
            100                 105                 110

Tyr Asn Arg Ala Pro Tyr Thr Phe Gly Gln Gly Thr Lys Val Glu Ile
        115                 120                 125

Lys Arg Thr Val Ala Ala Pro Ser Val Phe Ile Phe Pro Pro Ser Asp
        130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
    210                 215                 220

Ser Pro Val Thr Lys Ser Phe Asn Arg Gly Glu Cys
225                 230                 235

<210> SEQ ID NO 14
<211> LENGTH: 236
<212> TYPE: PRT
<213> ORGANISM: Artificial sequence
<220> FEATURE:
<223> OTHER INFORMATION: Laboratory synthesis

<400> SEQUENCE: 14

Met Asp Met Arg Val Pro Ala Gln Leu Leu Gly Leu Leu Leu Leu Trp
1               5                   10                  15

Leu Pro Asp Thr Arg Cys Asp Ile Gln Met Thr Gln Ser Pro Ser Ser
                20                  25                  30

Val Ser Ala Ser Val Gly Asp Arg Val Thr Ile Thr Cys Arg Ala Ser
            35                  40                  45

Gln Gly Ile Arg Asn Tyr Leu Ala Trp Tyr Gln Gln Lys Pro Gly Lys
        50                  55                  60
```

Ala Pro Lys Leu Leu Ile Tyr Ala Ala Ser Thr Leu Gln Ser Gly Val
65                  70                  75                  80

Pro Ser Arg Phe Ser Gly Ser Gly Ser Gly Thr Gly Phe Thr Leu Thr
                85                  90                  95

Ile Ser Ser Leu Gln Pro Glu Asp Phe Ala Thr Tyr Tyr Cys Gln Arg
            100                 105                 110

Tyr Asn Arg Ala Pro Tyr Thr Phe Gly Gln Gly Thr Lys Val Glu Ile
                115                 120                 125

Lys Arg Thr Val Ala Ala Pro Ser Val Phe Ile Phe Pro Pro Ser Asp
            130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
                180                 185                 190

Ser Thr Tyr Ser Leu Ser Ser Thr Leu Thr Leu Ser Lys Ala Asp Tyr
            195                 200                 205

Glu Lys His Lys Val Tyr Ala Cys Glu Val Thr His Gln Gly Leu Ser
210                 215                 220

Ser Pro Val Thr Lys Ser Phe Asn Arg Gly Glu Cys
225                 230                 235

<210> SEQ ID NO 15
<211> LENGTH: 236
<212> TYPE: PRT
<213> ORGANISM: Artificial sequence
<220> FEATURE:
<223> OTHER INFORMATION: Laboratory synthesis

<400> SEQUENCE: 15

Met Asp Met Arg Val Pro Ala Gln Leu Leu Gly Leu Leu Leu Leu Trp
1               5                   10                  15

Leu Pro Asp Thr Arg Cys Asp Ile Gln Met Thr Gln Ser Pro Ser Ser
                20                  25                  30

Val Ser Ala Ser Val Gly Asp Arg Val Thr Ile Thr Cys Arg Ala Ser
            35                  40                  45

Gln Gly Ile Arg Asn Tyr Leu Ala Trp Tyr Gln Gln Lys Pro Gly Lys
        50                  55                  60

Val Pro Val Leu Leu Ile Tyr Ala Ala Ser Thr Leu Gln Ser Gly Val
65                  70                  75                  80

Pro Ser Arg Phe Ser Gly Ser Gly Ser Gly Thr Gly Phe Thr Leu Thr
                85                  90                  95

Ile Ser Ser Leu Gln Pro Glu Asp Val Ala Thr Tyr Tyr Cys Gln Arg
            100                 105                 110

Tyr Asn Arg Ala Pro Tyr Thr Phe Gly Gln Gly Thr Lys Val Glu Ile
                115                 120                 125

Lys Arg Thr Val Ala Ala Pro Ser Val Phe Ile Phe Pro Pro Ser Asp
            130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
                180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
        210                 215                 220

Ser Pro Val Thr Lys Ser Phe Asn Arg Gly Glu Cys
225                 230                 235

<210> SEQ ID NO 16
<211> LENGTH: 174
<212> TYPE: PRT
<213> ORGANISM: Artificial sequence
<220> FEATURE:
<223> OTHER INFORMATION: Laboratory synthesis

<400> SEQUENCE: 16

Met Glu Leu Gly Leu Ser Trp Ile Phe Leu Leu Ala Ile Leu Lys Gly
1               5                   10                  15

Val Gln Cys Glu Val Gln Leu Val Glu Ser Gly Gly Gly Leu Val Gln
            20                  25                  30

Pro Gly Arg Ser Leu Arg Leu Ser Cys Ala Ala Ser Gly Phe Thr Phe
        35                  40                  45

Asp Asp Tyr Ala Met His Trp Val Arg Gln Ala Pro Gly Lys Gly Leu
    50                  55                  60

Glu Trp Val Ser Ala Ile Thr Trp Asn Ser Gly His Ile Asp Tyr Ala
65                  70                  75                  80

Asp Ser Val Glu Gly Arg Phe Thr Ile Ser Leu Asp Thr Ser Lys Ser
                85                  90                  95

Thr Ala Tyr Leu Gln Met Asn Ser Leu Arg Ala Glu Asp Ser Ala Val
            100                 105                 110

Tyr Tyr Cys Ala Lys Val Ser Tyr Leu Ser Thr Ala Ser Ser Leu Asp
        115                 120                 125

Tyr Trp Gly Gln Gly Thr Leu Val Thr Val Ser Ser Ala Ser Thr Lys
    130                 135                 140

Gly Pro Ser Val Phe Pro Leu Ala Pro Ser Ser Lys Ser Thr Ser Gly
145                 150                 155                 160

Gly Thr Ala Ala Leu Gly Cys Leu Val Lys Asp Tyr Phe Pro
                165                 170

<210> SEQ ID NO 17
<211> LENGTH: 174
<212> TYPE: PRT
<213> ORGANISM: Artificial sequence
<220> FEATURE:
<223> OTHER INFORMATION: Laboratory synthesis

<400> SEQUENCE: 17

Met Glu Leu Gly Leu Ser Trp Ile Phe Leu Leu Ala Ile Leu Lys Gly
1               5                   10                  15

Val Gln Cys Glu Val Gln Leu Val Glu Ser Gly Gly Gly Leu Val Gln
            20                  25                  30

Pro Gly Arg Ser Leu Arg Leu Ser Cys Ala Ala Ser Gly Phe Thr Phe
        35                  40                  45

Asp Asp Tyr Ala Met His Trp Val Arg Gln Ala Pro Gly Lys Gly Leu
    50                  55                  60

Glu Trp Val Ser Ala Ile Thr Trp Asn Ser Gly His Ile Asp Tyr Ala
65                  70                  75                  80

Asp Ser Val Glu Gly Arg Phe Thr Phe Ser Leu Asp Thr Ser Lys Ser

```
                  85                  90                  95

Thr Ala Tyr Leu Gln Met Asn Ser Leu Arg Ala Glu Asp Thr Ala Val
            100                 105                 110

Tyr Tyr Cys Ala Lys Val Ser Tyr Leu Ser Thr Ala Ser Ser Leu Asp
            115                 120                 125

Tyr Trp Gly Gln Gly Thr Leu Val Thr Val Ser Ser Ala Ser Thr Lys
    130                 135                 140

Gly Pro Ser Val Phe Pro Leu Ala Pro Ser Ser Lys Ser Thr Ser Gly
145                 150                 155                 160

Gly Thr Ala Ala Leu Gly Cys Leu Val Lys Asp Tyr Phe Pro
                165                 170

<210> SEQ ID NO 18
<211> LENGTH: 174
<212> TYPE: PRT
<213> ORGANISM: Artificial sequence
<220> FEATURE:
<223> OTHER INFORMATION: Laboratory synthesis

<400> SEQUENCE: 18

Met Glu Leu Gly Leu Ser Trp Ile Phe Leu Leu Ala Ile Leu Lys Gly
1               5                   10                  15

Val Gln Cys Glu Val Gln Leu Val Glu Ser Gly Gly Gly Leu Val Gln
                20                  25                  30

Pro Gly Gly Ser Leu Arg Leu Ser Cys Ala Ala Ser Gly Tyr Thr Phe
            35                  40                  45

Asp Asp Tyr Ala Met His Trp Val Arg Gln Ala Pro Gly Lys Gly Leu
    50                  55                  60

Glu Trp Val Ser Ala Ile Thr Trp Asn Ser Gly His Ile Asp Tyr Ala
65                  70                  75                  80

Asp Ser Val Glu Gly Arg Phe Thr Ile Ser Leu Asp Thr Ser Lys Ser
                85                  90                  95

Thr Ala Tyr Leu Gln Met Asn Ser Leu Arg Ala Glu Asp Ser Ala Val
            100                 105                 110

Tyr Tyr Cys Ala Lys Val Ser Tyr Leu Ser Thr Ala Ser Ser Leu Asp
            115                 120                 125

Tyr Trp Gly Gln Gly Thr Leu Val Thr Val Ser Ser Ala Ser Thr Lys
    130                 135                 140

Gly Pro Ser Val Phe Pro Leu Ala Pro Ser Ser Lys Ser Thr Ser Gly
145                 150                 155                 160

Gly Thr Ala Ala Leu Gly Cys Leu Val Lys Asp Tyr Phe Pro
                165                 170

<210> SEQ ID NO 19
<211> LENGTH: 174
<212> TYPE: PRT
<213> ORGANISM: Artificial sequence
<220> FEATURE:
<223> OTHER INFORMATION: Laboratory synthesis

<400> SEQUENCE: 19

Met Glu Leu Gly Leu Ser Trp Ile Phe Leu Leu Ala Ile Leu Lys Gly
1               5                   10                  15

Val Gln Cys Glu Val Gln Leu Val Glu Ser Gly Gly Gly Leu Val Gln
                20                  25                  30

Pro Gly Gly Ser Leu Arg Leu Ser Cys Ala Ala Ser Gly Tyr Thr Phe
            35                  40                  45
```

```
Asp Asp Tyr Ala Met His Trp Val Arg Gln Ala Pro Gly Lys Gly Leu
    50                  55                  60

Glu Trp Val Ser Ala Ile Thr Trp Asn Ser Gly His Ile Asp Tyr Ala
 65                 70                  75                  80

Asp Ser Val Glu Gly Arg Phe Thr Phe Ser Leu Asp Thr Ser Lys Ser
                85                  90                  95

Thr Ala Tyr Leu Gln Met Asn Ser Leu Arg Ala Glu Asp Thr Ala Val
            100                 105                 110

Tyr Tyr Cys Ala Lys Val Ser Tyr Leu Ser Thr Ala Ser Ser Leu Asp
        115                 120                 125

Tyr Trp Gly Gln Gly Thr Leu Val Thr Val Ser Ser Ala Ser Thr Lys
    130                 135                 140

Gly Pro Ser Val Phe Pro Leu Ala Pro Ser Ser Lys Ser Thr Ser Gly
145                 150                 155                 160

Gly Thr Ala Ala Leu Gly Cys Leu Val Lys Asp Tyr Phe Pro
                165                 170
```

<210> SEQ ID NO 20
<211> LENGTH: 174
<212> TYPE: PRT
<213> ORGANISM: Artificial sequence
<220> FEATURE:
<223> OTHER INFORMATION: Laboratory synthesis

<400> SEQUENCE: 20

```
Met Glu Leu Gly Leu Ser Trp Ile Phe Leu Leu Ala Ile Leu Lys Gly
  1               5                  10                  15

Val Gln Cys Glu Val Gln Leu Val Glu Ser Gly Gly Gly Leu Val Gln
             20                  25                  30

Pro Gly Gly Ser Leu Arg Leu Ser Cys Ala Ala Ser Gly Tyr Thr Phe
         35                  40                  45

Asp Asp Tyr Ala Met His Trp Val Arg Gln Ala Pro Gly Lys Gly Leu
    50                  55                  60

Glu Trp Val Ser Ala Ile Thr Trp Asn Ser Gly His Ile Asp Tyr Ala
 65                 70                  75                  80

Asp Ser Val Glu Gly Arg Phe Thr Ile Ser Leu Asp Thr Ser Val Ser
                85                  90                  95

Thr Ala Tyr Leu Gln Met Asn Ser Leu Arg Ala Glu Asp Ser Ala Val
            100                 105                 110

Tyr Tyr Cys Ala Lys Val Ser Tyr Leu Ser Thr Ala Ser Ser Leu Asp
        115                 120                 125

Tyr Trp Gly Gln Gly Thr Leu Val Thr Val Ser Ser Ala Ser Thr Lys
    130                 135                 140

Gly Pro Ser Val Phe Pro Leu Ala Pro Ser Ser Lys Ser Thr Ser Gly
145                 150                 155                 160

Gly Thr Ala Ala Leu Gly Cys Leu Val Lys Asp Tyr Phe Pro
                165                 170
```

<210> SEQ ID NO 21
<211> LENGTH: 714
<212> TYPE: DNA
<213> ORGANISM: Artificial sequence
<220> FEATURE:
<223> OTHER INFORMATION: Laboratory synthesis

<400> SEQUENCE: 21
atggacatga gggtccctgc tcagctcctg ggactcctgc tgctctggct cccagatacc      60

| | |
|---|---|
| agatgtgaca tccagatgac ccagtctcca tcctccctgt ctgcatctgt aggagacaga | 120 |
| gtcaccatca cttgccgggc gagtcagggc attaggaatt atttagcctg gtatcagcag | 180 |
| aaaccaggga aagctcctaa actcctgatc tatgctgcat ccactttgca atcaggggtc | 240 |
| ccatctcggt tcagcggcag tggatctggg acagatttca ctctcaccat cagcagcctg | 300 |
| cagcctgaag atgttgcaac ttattactgt caaaggtata cagagcccc gtacactttt | 360 |
| ggccagggga ccaaggtgga gatcaaacga actgtggctg caccatctgt cttcatcttc | 420 |
| ccgccatctg atgagcagtt gaaatctgga actgcctctg ttgtgtgcct gctgaataac | 480 |
| ttctatccca gagaggccaa agtacagtgg aaggtggata cgccctcca atcgggtaac | 540 |
| tcccaggaga gtgtcacaga gcaggacagc aaggacagca cctacagcct cagcagcacc | 600 |
| ctgacgctga gcaaagcaga ctacgagaaa cacaaagtct acgcctgcga agtcacccat | 660 |
| cagggcctga gctcgcccgt cacaaagagc ttcaacaggg gagagtgtta gtaa | 714 |

<210> SEQ ID NO 22
<211> LENGTH: 522
<212> TYPE: DNA
<213> ORGANISM: Artificial sequence
<220> FEATURE:
<223> OTHER INFORMATION: Laboratory synthesis

<400> SEQUENCE: 22

| | |
|---|---|
| atggagttgg gactgagctg gattttcctt ttggctattt taaaaggtgt ccagtgtgag | 60 |
| gtgcagctgg tggagtctgg gggaggcttg gtacagcccg gcaggtccct gagactctcc | 120 |
| tgtgcggcct ctggattcac ctttgatgat tatgccatgc actgggtccg gcaagctcca | 180 |
| gggaagggcc tggaatgggt ctcagctatc acttggaata gtggtcacat agactatgcg | 240 |
| gactctgtgg agggccgatt caccatctcc agagacaacg ccaagaactc cctgtatctg | 300 |
| caaatgaaca gtctgagagc tgaggatacg gccgtatatt actgtgcgaa agtctcgtac | 360 |
| cttagcaccg cgtcctccct tgactattgg ggccaaggaa ccctggtcac cgtctcgagt | 420 |
| gcctccacca agggcccatc ggtcttcccc ctggcaccct cctccaagag cacctctggg | 480 |
| ggcacagcag ccctgggctg cctggtcaag gactacttcc cc | 522 |

<210> SEQ ID NO 23
<211> LENGTH: 236
<212> TYPE: PRT
<213> ORGANISM: Artificial sequence
<220> FEATURE:
<223> OTHER INFORMATION: Laboratory synthesis

<400> SEQUENCE: 23

```
Met Asp Met Arg Val Pro Ala Gln Leu Leu Gly Leu Leu Leu Leu Trp
1               5                   10                  15

Leu Pro Asp Thr Arg Cys Asp Ile Gln Met Thr Gln Ser Pro Ser Ser
            20                  25                  30

Leu Ser Ala Ser Val Gly Asp Arg Val Thr Ile Thr Cys Arg Ala Ser
        35                  40                  45

Gln Gly Ile Arg Asn Tyr Leu Ala Trp Tyr Gln Gln Lys Pro Gly Lys
    50                  55                  60

Ala Pro Lys Leu Leu Ile Tyr Ala Ala Ser Thr Leu Gln Ser Gly Val
65                  70                  75                  80

Pro Ser Arg Phe Ser Gly Ser Gly Ser Gly Thr Asp Phe Thr Leu Thr
                85                  90                  95

Ile Ser Ser Leu Gln Pro Glu Asp Val Ala Thr Tyr Tyr Cys Gln Arg
```

```
            100                 105                 110
Tyr Asn Arg Ala Pro Tyr Thr Phe Gly Gln Gly Thr Lys Val Glu Ile
        115                 120                 125

Lys Arg Thr Val Ala Ala Pro Ser Val Phe Ile Phe Pro Pro Ser Asp
    130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
    210                 215                 220

Ser Pro Val Thr Lys Ser Phe Asn Arg Gly Glu Cys
225                 230                 235

<210> SEQ ID NO 24
<211> LENGTH: 174
<212> TYPE: PRT
<213> ORGANISM: Artificial sequence
<220> FEATURE:
<223> OTHER INFORMATION: Laboratory synthesis

<400> SEQUENCE: 24

Met Glu Leu Gly Leu Ser Trp Ile Phe Leu Leu Ala Ile Leu Lys Gly
1               5                   10                  15

Val Gln Cys Glu Val Gln Leu Val Glu Ser Gly Gly Gly Leu Val Gln
            20                  25                  30

Pro Gly Arg Ser Leu Arg Leu Ser Cys Ala Ala Ser Gly Phe Thr Phe
        35                  40                  45

Asp Asp Tyr Ala Met His Trp Val Arg Gln Ala Pro Gly Lys Gly Leu
    50                  55                  60

Glu Trp Val Ser Ala Ile Thr Trp Asn Ser Gly His Ile Asp Tyr Ala
65                  70                  75                  80

Asp Ser Val Glu Gly Arg Phe Thr Ile Ser Arg Asp Asn Ala Lys Asn
                85                  90                  95

Ser Leu Tyr Leu Gln Met Asn Ser Leu Arg Ala Glu Asp Thr Ala Val
            100                 105                 110

Tyr Tyr Cys Ala Lys Val Ser Tyr Leu Ser Thr Ala Ser Ser Leu Asp
        115                 120                 125

Tyr Trp Gly Gln Gly Thr Leu Val Thr Val Ser Ser Ala Ser Thr Lys
    130                 135                 140

Gly Pro Ser Val Phe Pro Leu Ala Pro Ser Ser Lys Ser Thr Ser Gly
145                 150                 155                 160

Gly Thr Ala Ala Leu Gly Cys Leu Val Lys Asp Tyr Phe Pro
                165                 170
```